US012728097B2

(12) United States Patent
Wu et al.

(10) Patent No.: US 12,728,097 B2
(45) **Date of Patent: *Sep. 8, 2026**

(54) DELAYED RELEASE ORAL PHARMACEUTICAL COMPOSITION

(71) Applicant: Aihol Corporation, Diamond Bar, CA (US)

(72) Inventors: Tsung-Chung Wu, Taipei City (TW); Yu-Chih Chen, Taipei City (TW)

(73) Assignee: Aihol COrporation, Diamond Bar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/399,068

(22) Filed: Nov. 24, 2025

(65) Prior Publication Data

US 2026/0090996 A1 Apr. 2, 2026

Related U.S. Application Data

(63) Continuation of application No. 18/904,150, filed on Oct. 2, 2024, now Pat. No. 12,521,351.

(51) Int. Cl.

| | |
|---|---|
| ***A61K 9/48*** | (2006.01) |
| ***A61K 9/00*** | (2006.01) |
| ***A61K 31/60*** | (2006.01) |
| ***A61K 31/728*** | (2006.01) |
| ***A61P 1/04*** | (2006.01) |

(52) U.S. Cl.

CPC .......... *A61K 9/4816* (2013.01); *A61K 9/0002* (2013.01); *A61K 9/0053* (2013.01); *A61K 9/4891* (2013.01); *A61K 31/60* (2013.01); *A61K 31/728* (2013.01); *A61P 1/04* (2018.01)

(58) Field of Classification Search

None

See application file for complete search history.

(56) References Cited

U.S. PATENT DOCUMENTS

| | | | | |
|---|---|---|---|---|
| 9,539,265 | B2 | 1/2017 | Chang | |
| 12,521,351 | B1 * | 1/2026 | Wu | A61K 9/4816 |
| 2011/0189271 | A1 | 8/2011 | Lad et al. | |

FOREIGN PATENT DOCUMENTS

| | | | |
|---|---|---|---|
| TW | 201434497 | A | 9/2014 |
| WO | 2014/142938 | A1 | 9/2014 |

OTHER PUBLICATIONS

Stevens et al., Controlled onset oral drug delivery: An opportunity for innovative life cycle management. American Pharmaceutical u Review . . . https://www.americanpharmaceuticalreview.com/Featured-Articles/163671-Controlled-Onset-Oral-Drug-Delivery-An-Opportunity-for-Innovative-life-cycle-manage.6/2014 (Year: 2014).

International Search report for PCT/US25/48913.

* cited by examiner

*Primary Examiner* — Aradhana Sasan

(74) *Attorney, Agent, or Firm* — patenttm.us

(57) ABSTRACT

Disclosed herein are compositions and methods for the treatment of inflammatory bowel disease. According to some embodiments, the compositions and methods involve the use of a delayed-release formulation containing a mesalamine layer, a hyaluronan layer, and at least one coating layer.

11 Claims, 1 Drawing Sheet

REPLACEMENT SHEET

DRAWINGS

DELAYED RELEASE ORAL PHARMACEUTICAL COMPOSITION

CROSS REFERENCE TO RELATED APPLICATIONS

The present application is a continuation application claiming priority under 35 U.S.C. § 120 from co-pending U.S. patent application Ser. No. 18/904,150, entitled DELAYED RELEASE ORAL PHARMACEUTICAL COMPOSITION, filed Oct. 2, 2024, the entire disclosure of which is incorporated by reference herein.

FIELD OF THE INVENTION

The present disclosure relates to delayed release pharmaceutical compositions and methods for treating and/or preventing inflammatory bowel disease (IBD) in a patient. In particular, the present disclosure relates to delayed release pharmaceutical compositions containing mesalamine and methods of using the same to treat and/or prevent IBD in a patient.

DESCRIPTION OF RELATED ART

Ulcerative colitis is a chronic inflammatory bowel disease (IBD) that causes inflammation and ulcers in the patient's digestive tract special in colon-rectal area. Ulcerative colitis affects the innermost lining of the patient's colon and rectum.

Mesalamine is also known as 5-aminosalicylate used for the treatment of patients with IBD includes ulcerative colitis (UC). Effective treatment for UC often requires delivering mesalamine to the affected areas in the colon or rectum. Traditionally, this has been achieved through oral and rectal administration, using either suppositories or enemas. However, rectal administration is generally less convenient and less acceptable to patients compared to oral administration. Additionally, suppositories only reach the rectum, while enemas typically cover only the left side of the colon, making these methods less effective for treating the right and transverse side of the colon.

Oral administration, on the other hand, has its limitation due to the absorption of mesalamine in the digestive tract before it reaches the colon or rectum. To address this, certain "delayed-release" or "extended-release" form of orally administered mesalamine have been developed. A delayed-release mesalamine formulation releases the medication specifically in the colon and/or rectum where it is most needed, while an extended-release mesalamine formulation releases the medication throughout the colon and rectal. There were five available mesalamine products approved by the United States Food and Drug Administration (FDA) for oral administration: APRISO® (Extended-Release Capsule), ASACOL HD® (Delayed-Release Tablet), DELZICOL® (Delayed-Release Capsule), LIALDA® (Delayed-Release Tablet), PENTASA® (Extended-Release Capsule). However, these oral mesalamine products have their drawbacks. For one thing, the DELZICOL® and LIALDA® capsules are approximately 25.3 and 23.4 millimeters, which may be difficult for some patients, such as pediatric patients or those with swallowing difficulties, to swallow. Additionally, delayed-release products like ASACOL HD®, DELZICOL®, and PENTASA are typically administered at least three times per day with a total dose of at least 2 grams per day, which may result in poor patient compliance. Therefore, current oral mesalamine formulations still suffer from sub-optimal drug release profiles and bioavailability, which can limit their therapeutic efficacy in treating chronic conditions such as ulcerative colitis.

In view of the above, there exists a need in the related art to provide a delayed release pharmaceutical compositions with a desirable pharmacokinetic profile that may promote patient compliance.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In one aspect, the present disclosure is directed to a delayed-release formulation. The present delayed-release formulation is advantageous in providing a desirable pharmacokinetic to improve the delivery and bioavailability of active ingredient. The present delayed-release formulation is also advantageous in having a more compact size, thereby enhancing patient compliance.

According to certain embodiments, the present delayed-release formulation includes a plurality of particles contained within the capsule shell, wherein each particle includes: (a) an inert core, in an amount of about 10-20 wt % of the particle; (b) a mesalamine layer applied to the surface of the inert core, wherein the mesalamine layer is in an amount of about 40-65 wt % of the particle and comprises mesalamine in an amount of about 80-99 wt % of the mesalamine layer; (c) a hyaluronan layer applied to the surface of the mesalamine layer, wherein the hyaluronan layer is in an amount of about 3-15 wt % of the particle and includes hyaluronic acid or a pharmaceutically-acceptable salt thereof in an amount of about 51-70 wt % of the hyaluronan layer; and (d) at least one coating layer applied to the surface of the hyaluronan layer, wherein the at least one coating layer is in an amount of about 15-30 wt % of the particle.

According to various embodiments of the present disclosure, the plurality of particles can be filled in capsules, pouches, packets, sachets, bottles, or blister packs.

According to certain embodiments of the present disclosure, the inert core includes a filler.

According to certain embodiments of the present disclosure, the mesalamine further layer includes at least one binder in an amount of about 0.5-15 wt % of the mesalamine layer.

According to certain embodiments of the present disclosure, the hyaluronan layer further includes at least one binder in an amount of about 30-49 wt % of the hyaluronan layer.

According to certain embodiments of the present disclosure, the hyaluronan layer includes a high-molecular weight of hyaluronic acid or the pharmaceutically-acceptable salt thereof and a low-molecular weight of hyaluronic acid or the pharmaceutically-acceptable salt thereof in an amount of about 1:5 to 5:1. In particular, the high-molecular weight of hyaluronic acid or the pharmaceutically-acceptable salt thereof has a viscosity average molecular weight (Mv) of 2000 kDa to 2500 kDa, and the low-molecular weight of hyaluronic acid or the pharmaceutically-acceptable salt thereof has an Mv of 300 kDa to 500 kDa.

According to certain embodiments of the present disclosure, the at least one coating layer includes an enteric coating layer, including one or more copolymer.

According to certain embodiments of the present disclosure, the enteric coating layer further includes at least one plasticizer.

According to certain embodiments of the present disclosure, the at least one coating layer further includes an isolation layer between the hyaluronan layer and the enteric coating layer, and including one or more copolymer.

According to certain embodiments of the present disclosure, the isolation layer further includes at least one plasticizer.

According to certain embodiments of the present disclosure, the delayed-release formulation can be formulated into a unit-dose form, for example, a capsule, a sachet, and the like, containing the plurality of particles to simplify the administration of the delayed-release formulation.

For example, the delayed-release formulation can be formulated as a delayed-release capsule containing 200 mg mesalamine, which provides a mean peak plasma concentration of mesalamine ($C_{max}$) of at least 400 ng/ml, following oral administration of the delayed-release capsule into a human as a single dose of two capsules each containing 200 mg mesalamine.

According to certain embodiments of the present disclosure, the delayed-release capsule provides a mean mesalamine plasma area under the curve from 6-12 hours ($AUC_{6-12}$) of at least 600 ng*hr/mL, following oral administration of the delayed-release capsule into a human as a single dose of two capsules each containing 200 mg mesalamine.

According to certain embodiments of the present disclosure, the delayed-release capsule provides a mean $AUC_{0-t}$ of at least 1,800 ng/ml, following oral administration of the delayed-release capsule into a human as a single dose of two capsules each containing 200 mg mesalamine.

According to certain embodiments of the present disclosure, the inert core is in an amount of 60 mg to 100 mg per capsule, the mesalamine layer is in an amount of 100 to 450 mg per capsule; the hyaluronan layer is in an amount of 30 mg to 60 mg per capsule; and the least one enteric coating is in an amount of 80 mg to 100 mg per capsule.

In another example, the delayed-release formulation can be formulated as a sachet or blister pack containing 200 mg to 4,800 mg mesalamine, such as 200, 400, 600, 800, 1,000, 1,200, 1,600, 2,000, 2,400, 3,000, 3,200, 3,600, 4,000, 4,200, or 4,800 mg mesalamine.

In another aspect, the present disclosure is directed to a method for treating and/or prevent IBD in a patient in need thereof using the foregoing delayed-release formulations, such that, following oral administration of the delayed-release formulation, the formulation is capable of providing the desired pharmacokinetic profile in the patient.

According to some embodiments of the present disclosure, the method comprises the step of administering to the patient an effective amount of the present delayed-release formulation.

Subject matters that are also included in other aspects of the present disclosure include the use of the present delayed-release formulations in the manufacture of a medicament for use in the prevention and/or treatment of IBD, as well as delayed-release formulations for use in the prevention and/or treatment of IBD.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

DESCRIPTION

Figure 1A:
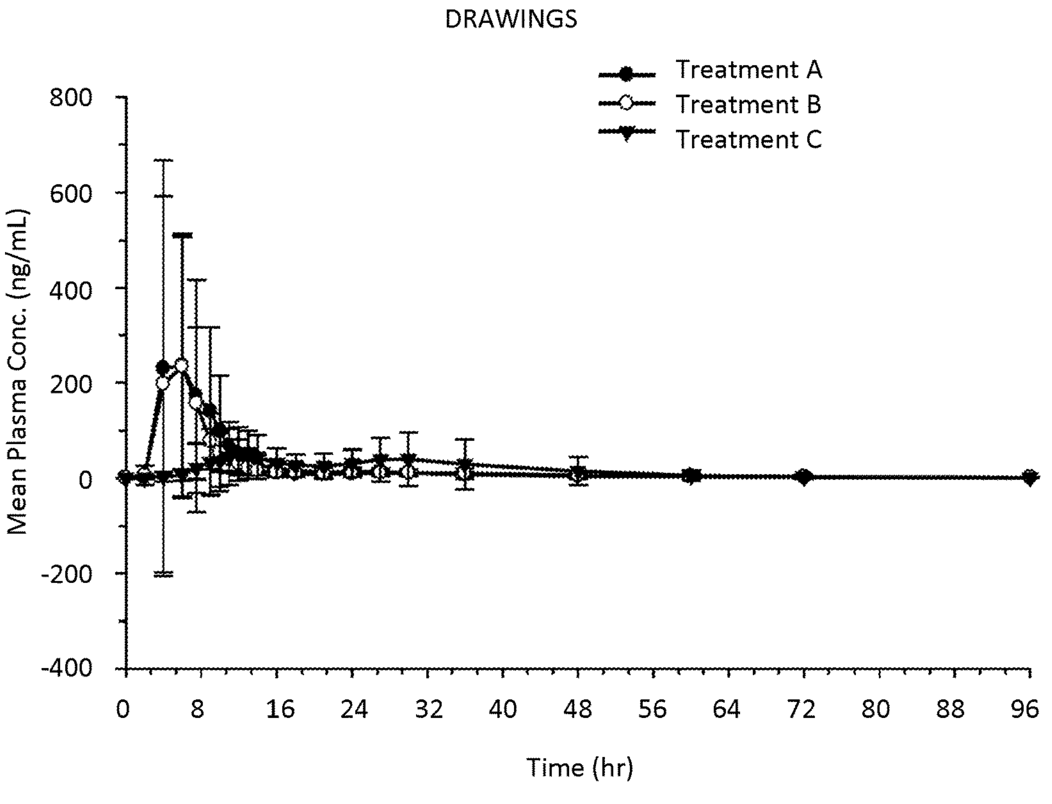
FIG. 1A and FIG. 1B shows the mean plasma mesalamine concentration vs. time profile of Treatment A, Treatment B, and Treatment C administered to 30 healthy human subjects in fasting conditions, in the linear scale and log scale, respectively.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

The terms "treatment" and "treating" as used herein may refer to a preventative (e.g., prophylactic), curative or palliative measure. In particular, the term "treating" as used herein refers to the application or administration of the present delayed-release formulations to a subject, who has a medical condition, a symptom associated with the medical condition, a disease or disorder secondary to the medical condition, or a predisposition toward the medical condition, with the purpose to partially or completely alleviate, ameliorate, relieve, delay onset of, inhibit progression of, reduce severity of, and/or reduce incidence of one or more symptoms or features of said particular disease, disorder, and/or condition associated with inflammatory bowel disease. Treatment may be administered to a subject who does not exhibit signs of a disease, disorder, and/or condition, and/or to a subject who exhibits only early signs of a disease, disorder and/or condition, for the purpose of decreasing the risk of developing pathology associated with the disease, disorder and/or condition.

The terms "subject" and "patient" are used interchangeably herein and are intended to mean an animal including the human species that is treatable by the delayed-release formulations and/or method of the present invention. The term "subject" or "patient" intended to refer to both the male and female gender unless one gender is specifically indicated.

The terms "application" and "administration" are used interchangeably herein to mean the application of the delayed-release formulations of the present invention to a subject in need of a treatment thereof.

The term "effective amount" as used herein refers to the quantity of the present delayed-release formulation that is sufficient to yield a desired therapeutic response. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two, or more doses in a suitable form to be administered at one, two or more times throughout a designated time period. The specific effective or sufficient amount will vary with such factors as particular condition being treated, the physical condition of the patient (e.g., the patient's body mass, age, or gender), the type of mammal or animal being treated, the duration of the treatment, the nature of concurrent therapy (if any), and the specific formulations employed and the structure of the therapeutic agent or its derivatives. Effective amount may be expressed, for example, as the total mass of the hyaluronan-drug conjugate (or the equivalent amount of the drug), e.g., in grams, milligrams or micrograms, or an effective concentration of the hyaluronan-drug conjugate in the final formulation, e.g., as milligrams per milliliter (mg/mL).

The phrase "pharmaceutically acceptable excipient" as used herein means a pharmaceutically acceptable material, composition or vehicle, such as a liquid, diluent, carrier, solvent, involved in carrying or transporting the subject agents from one organ or portion of the body, to another organ or portion of the body. Each excipient must be "acceptable" in the sense of being compatible with the other ingredients of the formulation. The pharmaceutical formulation contains the active substance of the invention in combination with one or more pharmaceutically acceptable ingredients. Preferably, the excipient can be in the form of a liquid diluent. These pharmaceutical preparations are a further object of the invention. Usually, the amount of active substance is between 0.1-95% by weight of the preparation, preferably between 0.2-20% by weight in preparations for parenteral use or for topical administration. For the clinical use of the methods of the present invention, the pharmaceutical composition of the invention is formulated into formulations suitable for the intended route of administration.

As used herein, the term "hyaluronic acid" (HA) (also called hyaluronate or hyaluronan) is an anionic, nonsulfated glycosaminoglycan composed of at least one disaccharide unit, specifically a D-glucuronic acid and an N-acetyl-D-glucosamine (-4GlcUAβ1-3GlcNAcβ1-). The molecular of HA can range from 379 Daltons (Da) (a single HA monomer) to millions of Daltons. Salts of hyaluronic acid include sodium hyaluronate, potassium hyaluronate, and the like. The term "HA derivative" refers to an HA having any modification on the hydroxyl, carboxyl, amide, or acetylamino groups of one or more disaccharide units of the HA.

According to the present disclosure, $T_{max}$ means "time to peak concentration," which is the time required to reach the peak plasma concentration of a drug after oral administration ($C_{max}$); $t_{1/2}$ means "biological half-time," which is the time required for the concentration of the drug to reach half of its original value; whereas $T_{lag}$ means "lag time," which is the time from administration of a drug to first quantifiable concentration. Furthermore, AUC means "area under the curve," which is the integral of the concentration-time curve (after a single dose or in steady state). In particular, $AUC_{0-t}$ is the area under the curve from time zero to the last non-zero concentration, calculated using the linear trapezoidal method; $AUC_{refTmax}$ is the area under the concentration-time curve from time zero to the time of the maximum concentration of the reference product (corresponding to the median $T_{max}$ of the Reference product), calculated using the linear trapezoidal method; and $AUC_{0-inf}$ is the area under the curve from time zero to infinity (extrapolated), calculated as $AUC_{0-t}+C_t/K_{el}$, where $C_t$ is the last observed non-zero concentration.

The present disclosure is based, at least in part, on the discovery that the delayed-release formulations described herein improve mesalamine bioavailability to a surprising and unexpected extent. In particular, these formulations include a hyaluronan layer that plays a critical role in modulating the release profile and protecting mesalamine during transit through the gastrointestinal (GI) tract. The inclusion of hyaluronan of different molecular weights enables further fine-tuning of the release profile. As a result, the formulation delivers higher and more sustained concentrations of mesalamine in the bloodstream, as evidenced by elevated $C_{max}$ (peak plasma concentration) and AUC (area under the curve) values, indicating enhanced absorption and prolonged therapeutic effect.

Additionally, the delayed-release mechanism, supported by the multi-layered structure of the particles, ensures that the mesalamine is released primarily in the intestinal tract, rather than in the stomach. This not only minimizes potential side effects such as gastric irritation but also maximizes the local therapeutic action of mesalamine in inflamed areas of the colon, where it is most needed.

In summary, the ability of this formulation to release mesalamine in a controlled, sustained manner improves the treatment regimen for patients, particularly those suffering from chronic bowel conditions like ulcerative colitis. It does so by maintaining effective drug concentrations over a longer period, thus enhancing both efficacy and patient outcomes.

In view of the foregoing, the present disclosure also proposes methods for preventing and/or treating inflammatory bowel disease by orally administering the present delayed-release formulations. Also provided herein is the use of said delayed-release formulations in the prevention and/or treatment of inflammatory bowel disease, as well as its use in the manufacture of a medicament for said treatment purpose. The medicament (i.e., a pharmaceutical composition) is, of course, a subject matter covered by the scope of the present application.

In one aspect, the present disclosure is directed to a delayed-release formulation. The present delayed-release formulation is advantageous in providing a desirable pharmacokinetic to improve the delivery and bioavailability of active ingredient. The present delayed-release formulation is also advantageous in having a more compact size, thereby enhancing patient compliance.

According to certain embodiments, the present delayed-release formulation includes a plurality of particles, wherein each particle includes: (a) an inert core, in an amount of about 10-20 wt % of the particle; (b) a mesalamine layer applied to the surface of the inert core, wherein the mesalamine layer is in an amount of about 40-65 wt % of the particle and comprises mesalamine in an amount of about 80-99 wt % of the mesalamine layer; (c) a hyaluronan layer applied to the surface of the mesalamine layer, wherein the hyaluronan layer is in an amount of about 3-15 wt % of the particle and includes hyaluronic acid or a pharmaceutically-acceptable salt thereof in an amount of about 51-70 wt % of the hyaluronan layer; and (d) at least one coating layer applied to the surface of the hyaluronan layer, wherein the at least one coating layer is in an amount of about 15-30 wt % of the particle.

As could be appreciated, the main ingredients such as mesalamine and hyaluronic acid or a pharmaceutically-acceptable salt thereof can be formulated, together with suitable pharmaceutically-acceptable excipients, into a multi-layered formulation suitable for oral administration.

The term "inert core" as used herein, refers to a pharmaceutically acceptable inert substrate which is routinely used in formulation art, that includes, but are not limited to, powder or a multiparticulate such as a granule, a pellet, a bead, a spherule, a beadlet, a millisphere, a nanosphere, a microsphere or a minitablet. According to certain embodiments of the present disclosure, the inert core includes a filler. Examples of fillers include but are not limited to, sugar, microcrystalline cellulose, vegetable gums, and waxes. In one embodiment, the filler of the inert core is microcrystalline cellulose. The inert cores may be prepared with the techniques known to a person skilled in the art, such as, wet granulation, dry granulation, or extrusion-spheronization and the like.

The inert core can be comprised in the particle, in an amount, for example, ranging from about 10 wt % to 20 wt %, 11 wt % to 19 wt %, 12 wt % to 18 wt %, 13 wt % to 17 wt %, 14 wt % to 16 wt %, 15 wt % to 18 wt %, or 17 wt % to 19 wt %, based on the total weight of the particle. More specifically, the inert core can be comprised in the particle in an amount of about 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, 15, 15.1, 15.2, 15.3, 15.4, 15.5, 15.6, 15.7, 15.8, 15.9, 16, 16.1, 16.2, 16.3, 16.4, 16.5, 16.6, 16.7, 16.8, 16.9, 17, 17.1, 17.2, 17.3, 17.4, 17.5, 17.6, 17.7, 17.8, 17.9, 18, 18.1, 18.2, 18.3, 18.4, 18.5, 18.6, 18.7, 18.8, 18.9, 19, 19.1, 19.2, 19.3, 19.4, 19.5, 19.6, 19.7, 19.8, 19.9, or 20 wt %, based on the total weight of the particle.

The mesalamine layer can be comprised in the particle, in an amount, for example, ranging from about 40 wt % to 65 wt %, 45 wt % to 60 wt %, or 50 wt % to 55 wt %, based on the total weight of the particle. More specifically, the mesalamine layer can be comprised in the particle in an amount of about 40, 41, 42, 43, 44, 45, 46, 47, 48, 49, 50, 51, 52, 53, 54, 55, 56, 57, 58, 59, 60, 61, 62, 63, 64, or 65 wt %, based on the total weight of the particle.

Mesalamine is the main ingredient of the mesalamine layer. Specifically, mesalamine can be comprised in the mesalamine layer, in an amount, for example, ranging from about 80 wt % to 99 wt %, 82 wt % to 97 wt %, 84 wt % to 95 wt %, 86 wt % to 93 wt %, or 88 wt % to 91 wt %, based on the total weight of the mesalamine layer. More specifically, mesalamine can be comprised in the mesalamine layer in an amount of 80, 81, 82, 83, 84, 85, 86, 87, 88, 89, 90, 91, 92, 93, 94, 95, 96, 97, 98, or 99 wt %, based on the total weight of the mesalamine layer.

In addition to mesalamine, the mesalamine layer may further include excipients such as at least one binder.

Examples of binder suitable for use in the mesalamine layer include but are not limited to, hydroxypropyl methylcellulose, hydroxypropyl cellulose and carboxymethyl-cellulose sodium, povidone, copolyvidone magnesium stearate, calcium stearate, zinc stearate; stearic acid, hydrogenated vegetable oil, hydrogenated castor oil, glyceryl palmitostearate, glyceryl behenate, polyethylene glycols, corn starch, sodium stearyl fumarate, sodium benzoate, mineral oil, talc, colloidal silicon dioxide, magnesium trisilicate, powdered cellulose, starch, tribasic calcium phosphate and the like or mixtures thereof. In one embodiment, the binder used in the mesalamine layer includes hydroxypropyl methylcellulose and talc.

The binder can be comprised in the mesalamine layer, in an amount, for example, ranging from about 0.5 wt % to 15 wt %, 1 wt % to 14.5 wt %, 2 wt % to 14 wt %, 3 wt % to 13.5 wt %, 4 wt % to 13 wt %, 5 wt % to 12.5 wt %, 6 wt % to 12 wt %, or 6.5 wt % to 11.5 wt %, based on the total weight of the mesalamine layer. More specifically, the binder can be comprised in the mesalamine layer in an amount of 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, or 15 wt %, based on the total weight of the mesalamine layer.

The hyaluronan layer can be comprised in the particle, in an amount, for example, ranging from about 3 wt % to 15 wt %, 4 wt % to 14 wt %, 5 wt % to 13 wt %, 6 wt % to 12 wt %, 7 wt % to 11 wt %, or 8 wt % to 10 wt %, based on the total weight of the particle. More specifically, the hyaluronan layer can be comprised in the particle in an amount of about 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, or 15 wt %, based on the total weight of the particle.

The main ingredient of the hyaluronan layer is hyaluronic acid or a pharmaceutically-acceptable salt thereof. Specifically, the hyaluronic acid or the pharmaceutically-acceptable salt thereof can be comprised in the hyaluronan layer, in an amount, for example, ranging from about 51 wt % to 70 wt %, 53 wt % to 68 wt %, 55 wt % to 66 wt %, or 57 wt % to 64 wt %, based on the total weight of the hyaluronan layer. More specifically, the hyaluronic acid or the pharmaceutically-acceptable salt thereof can be comprised in the hyaluronan layer in an amount of 51, 52, 53, 54, 55, 56, 57, 58, 59, 60, 61, 62, 63, 64, 65, 66, 67, 68, 69, or 70 wt %, based on the total weight of the mesalamine layer.

According to certain embodiments of the present disclosure, the hyaluronan layer includes both high-molecular weight hyaluronic acid (HMWHA) and low-molecular weight hyaluronic acid (LMWHA) or a pharmaceutically-acceptable salt thereof. In certain embodiments of the present disclosure, that HMWHA has a viscosity average molecular weight (Mv) of 2000 kDa to 2500 kDa, and the LMWHA has an Mv of 300 kDa to 500 kDa. More specifically, the Mv of the HMWHA is 2, 2.01, 2.02, 2.03, 2.04, 2.05, 2.06, 2.07, 2.08, 2.09, 2.1, 2.11, 2.12, 2.13, 2.14, 2.15, 2.16, 2.17, 2.18, 2.19, 2.2, 2.21, 2.22, 2.23, 2.24, 2.25, 2.26, 2.27, 2.28, 2.29, 2.3, 2.31, 2.32, 2.33, 2.34, 2.35, 2.36, 2.37, 2.38, 2.39, 2.4, 2.41, 2.42, 2.43, 2.44, 2.45, 2.46, 2.47, 2.48, 2.49, or 2.5 million daltons, whereas the Mv of the LMWHA is 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, or 0.5 million daltons. In one embodiment, the hyaluronan layer includes HMWHA having the Mv of 2.18 million daltons and LMWHA having the Mv of 0.38 million daltons.

According to certain embodiments of the present disclosure, the HMWHA and LMWHA can be comprised in the hyaluronan layer in an amount ranging from 1:5 to 5:1. For example, the HMWHA and LMWHA may be in an amount of 1:5, 1:4, 1:3, 1:2, 1:1, 2:1, 3:1, 4:1, or 5:1.

In addition to HMWHA and LMWHA, the hyaluronan layer may further include excipients such as at least one binder. In one embodiment, the hyaluronan layer includes HMWHA and LMWHA in a weight ratio of 4:1.

According to certain embodiments of the present disclosure, the hyaluronan layer further includes at least one binder in an amount of 30 to 49 wt % of the hyaluronan layer. The binder suitable for use in the hyaluronan layer may be any of the binders described above for the mesalamine layer. In various embodiments, the binder used in the hyaluronan layer may be the same as or different from that used in the mesalamine layer. In one embodiment, the binder used in the hyaluronan layer includes low-substituted hydroxypropyl cellulose.

The binder can be comprised in the hyaluronan layer, in an amount, for example, ranging from about 30 wt % to 49 wt %, 32 wt % to 45 wt %, or 34 wt % to 43 wt %, based on the total weight of the hyaluronan layer. More specifically, the binder can be comprised in the hyaluronan layer in an amount of about 30, 31, 32, 33, 34, 35, 36, 37, 38, 39, 40, 41, 42, 43, 44, 45, 46, 47, 48, 49 wt %, based on the total weight of the hyaluronan layer.

The coating layer is designed to ensure the delayed release, allowing the mesalamine to pass through the stomach and reach the lower parts of the GI tract, where it can be more effectively absorbed. The coating layer can be comprised in the particle, in an amount, for example, ranging from about 15 wt % to 30 wt %, 17 wt % to 28 wt %, 19 wt % to 26 wt %, or 21 wt % to 24 wt %, based on the total weight of the particle. More specifically, the coating layer can be comprised in the particle in an amount of about 15, 16, 17, 18, 19, 20, 21, 22, 23, 24, 25, 26, 27, 28, 29, or 30 wt %, based on the total weight of the particle.

According to certain embodiments of the present disclosure, the at least one coating layer includes an enteric coating layer, which is insoluble in gastric juice and soluble in intestinal juice at a pH >5. The enteric coating layer can be comprised in the particle, in an amount, for example, ranging from about 15 wt % to 20 wt %, 16 wt % to 19.5 wt %, or 17 wt % to 19 wt %, based on the total weight of the particle. More specifically, the enteric coating layer can be comprised in the particle in an amount of about 15, 15.1, 15.2, 15.3, 15.4, 15.5, 15.6, 15.7, 15.8, 15.9, 16, 16.1, 16.2, 16.3, 16.4, 16.5, 16.6, 16.7, 16.8, 16.9, 17, 17.1, 17.2, 17.3, 17.4, 17.5, 17.6, 17.7, 17.8, 17.9, 18, 18.1, 18.2, 18.3, 18.4, 18.5, 18.6, 18.7, 18.8, 18.9, 19, 19.1, 19.2, 19.3, 19.4, 19.5, 19.6, 19.7, 19.8, 19.9, or 20 wt %, based on the total weight of the particle.

The enteric coating layer preferably includes one or more copolymer. Examples of copolymers suitable for use in the enteric coating layer include, but are not limited to, a methyl acrylate-methyl methacrylate-methacrylic acid copolymer, a methacrylic acid-methyl methacrylate copolymer, a methacrylic acid-ethyl acrylate copolymer, and a methacrylic acid-ethyl acetate copolymer. In one embodiment, the enteric coating layer includes the copolymer based on methyl acrylate, methyl methacrylate and methacrylic acid and a copolymer based on methacrylic acid and ethyl acrylate.

The copolymer may be comprised in the enteric coating layer, in an amount, for example, ranging from about 75 wt % to 98 wt %, 80 wt % to 96 wt %, or 85 wt % to 94 wt %, based on the total weight of the enteric coating layer. More specifically, the copolymer may be comprised in the enteric coating layer in an amount of about 76, 77, 78, 79, 80, 81, 82, 83, 84, 85, 86, 87, 88, 89, 90, 91, 92, 93, 94, 95, 96, 97, or 98 wt %, based on the total weight of the enteric coating layer.

According to certain optional embodiments of the present disclosure, the enteric coating layer further includes at least one plasticizer. Examples of plasticizers suitable for use in the enteric coating layer include, but are not limited to, acetyltributyl citrate, acetyltriethyl citrate, benzyl benzoate, cellulose acetate phthalate, chlorbutanol, dextrin, dibutyl phthalate, dibutyl secacate, diethyl phthalate, dimethyl phthalate, glycerin, glycerin monostearate, hypromellose phthalate, mannitol, mineral oil an lanolin alcohols, palmitic acid, polyethylene glycol, polyvinyl acetate phthalate, propylene glycol, 2-pyrrolidone, sorbitol, stearic acid, triacetin, tributyl citrate, triethanolamine, and triethyl citrate. In one embodiment, the plasticizer used in the enteric coating layer includes triethyl citrate, glycerin monostearate, and sorbitol.

The plasticizer may be comprised in the enteric coating layer, in an amount, for example, ranging from about 2 wt % to 25 wt %, 5 wt % to 20 wt %, or 10 wt % to 15 wt %, based on the total weight of the enteric coating layer. More specifically, the plasticizer may be comprised in the enteric coating layer in an amount of about 2, 3, 4, 5, 6, 7, 8, 9, 10, 11, 12, 13, 14, 15, 16, 17, 18, 19, 20, 21, 22, 23, or 24 wt %, based on the total weight of the enteric coating layer.

According to certain embodiments of the present disclosure, the at least one coating layer further includes an isolation layer between the hyaluronan layer and the enteric coating layer. The isolation layer preferably includes one or more copolymer. Examples of copolymers suitable for use in the isolation layer include, but are not limited to, a methacrylic acid-methyl methacrylate copolymer, methacrylic acid-methacrylate copolymer, and a methacrylic acid-ethylacrylate copolymer. In one embodiment, the isolation layer includes the copolymer based on methacrylic acid and methyl methacrylate.

The copolymer may be comprised in the isolation layer, in an amount, for example, ranging from about 51 wt % to 70 wt %, or 55 wt % to 60 wt %, based on the total weight of the isolation layer. More specifically, the copolymer may be comprised in the isolation layer in an amount of about 51, 52, 53, 54, 55, 56, 57, 58, 59, 60, 61, 62, 63, 64, 65, 66, 67, 68, 69, or 70 wt %, based on the total weight of the isolation layer.

According to certain embodiments of the present disclosure, the isolation layer further includes at least one plasticizer. The plasticizer suitable for use in the isolation layer may be any of the plasticizers described above for the enteric coating layer. In various embodiments, the plasticizer used in the isolation layer may be the same as or different from that used in the enteric coating layer. In one embodiment, the plasticizer used in the isolation layer includes triethyl citrate.

The plasticizer can be comprised in the isolation layer, in an amount, for example, ranging from about 30 wt % to 49 wt %, 32 wt % to 45 wt %, or 34 wt % to 40 wt %, based on the total weight of the isolation layer. More specifically, the plasticizer can be comprised in the isolation layer in an amount of about 30, 31, 32, 33, 34, 35, 36, 37, 38, 39, 40, 41, 42, 43, 44, 45, 46, 47, 48, 49 wt %, based on the total weight of the isolation layer. In another embodiment, the isolation layer further includes talc.

According to certain optional embodiments, the delayed-release formulation can be filled in capsules, pouches, packets, sachets, bottles, or blister packs to simplify the administration of the delayed-release formulation. Optionally, the delayed-release formulation can be formulated into a unit-dose form, such as tablets, capsules, pouches, packets, sachets, bottles, and blister packs, wherein the unit dose form contains a specific dose of mesalamine in particle form.

According to some optional embodiment of the present disclosure, the desired amount of multi-layered particles are encapsulated in a two-piece hard gelatin capsule using a capsule machine. For example, the multi-layered particles are encapsulated in a capsule such that the amount of mesalamine is about 200 mg per capsule. According to certain embodiment, the capsule is a size 0 capsule having a length of 21.6 millimeters.

According to certain embodiments of the present disclosure, the inert core is in an amount of 60 to 100 mg per capsule, the mesalamine layer is in an amount of 100 to 450 mg per capsule; the hyaluronan layer is in an amount of 30 to 60 mg per capsule; and the least one enteric coating is in an amount of 80 to 100 mg per capsule.

Optionally, mesalamine can be comprised in each capsule in an amount of 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, or 400 mg.

Optionally, hyaluronan can be comprised in each capsule in an amount of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 mg.

According to certain embodiments of the present disclosure, the delayed-release capsule provides a mean peak plasma concentration of mesalamine ($C_{max}$) of at least 400 ng/ml, following oral administration of the delayed-release capsule into a human as a single dose of two capsules each containing 200 mg mesalamine.

According to certain optional embodiments, the delayed-release capsule provides a mean $C_{max}$ ranging from 400 to 600 ng/ml, 410 to 550 ng/ml, 420 to 500 ng/ml, or 430 to 450 ng/ml.

According to certain embodiments of the present disclosure, the delayed-release capsule provides a mean mesalamine plasma area under the curve from 6-12 hours ($AUC_{6-12}$) of at least 600 ng*hr/mL, following oral administration of the delayed-release capsule into a human as a single dose of two capsules each containing 200 mg mesalamine.

According to certain optional embodiments, the delayed-release capsule provides a mean $AUC_{6-12}$ ranging from 600 to 1,000 ng/ml, 650 to 950 ng/ml, 700 to 900 ng/ml, or 750 to 850 ng/ml.

According to certain embodiments of the present disclosure, the delayed-release capsule provides a mean $AUC_{0-t}$ of at least 1,800 ng/ml, following oral administration of the delayed-release capsule into a human as a single dose of two capsules each containing 200 mg mesalamine.

According to certain optional embodiments, the delayed-release capsule provides a mean $AUC_{0-t}$ ranging from 1,800 to 2,500 ng/ml, 1,900 to 2,400 ng/ml, or 2,000 to 2,300 ng/ml.

According to some optional embodiment of the present disclosure, the plurality of particles are packaged into a sachet, blister pack, or the like, such that the formulation achieves a pharmacokinetic profile equivalent to that provided by the delayed-release capsules. For example, wherein each sachet or blister pack may contain 200 mg to 4,800 mg mesalamine, such as 200, 400, 600, 800, 1,000, 1,200, 1,600, 2,000, 2,400, 3,000, 3,200, 3,600, 4,000, 4,200, or 4,800 mg mesalamine.

In another aspect, the present disclosure is directed to a method for treating and/or prevent IBD in a patient in need thereof using the foregoing delayed-release formulations, such that, following oral administration of the delayed-release formulation, the formulation is capable of providing the desired pharmacokinetic profile in the patient.

According to some embodiments of the present disclosure, the method comprises the step of administering to the patient an effective amount of the present delayed-release formulation.

In certain embodiments, the delayed-release formulation is administered twice per day as a single dose of two delayed-release capsules each containing 200 mg mesalamine.

In certain embodiments, the delayed-release formulation is provided in the form of a sachet, blister pack, or the like, and is administered once, twice, three times or four times per day. In certain embodiments, the delayed-release formulation provided as a sachet or blister pack is administered at a daily dose between 800 to 4,800 mg mesalamine, such as 800, 1,200, 1,600, 2,000, 2,400, 3,2000, 3,600, 4,000, or 4,800 mg of mesalamine, wherein the daily dose can be provided in a single sachet or blister pack or multiple sachets or blister packs.

Yet another aspect of the present disclosure is direct to the use of a delayed-release formulation in the manufacture of a medicament for use in the treatment of inflammatory bowel disease. Still another aspect of the present disclosure is direct to the use of a delayed-release formulation in the treatment of inflammatory bowel disease. Similarly, the various dosing regimens (including dosages and dosing intervals) concerning the delayed-release formulation are also applicable in these aspects.

The following discussion is provided to elucidate certain aspects of the present invention and to aid those of skilled in the art in practicing this invention. This discussion is in no way to be considered to limit the scope of the invention in any manner. Without further elaboration, it is believed that one skilled in the art can, based on the description herein, utilize the present invention to its fullest extent.

Summary of Clinical Trial Design

A phase I clinical trial was conducted to study the rate and extent of absorption of three interventions: Treatment A: mesalamine-sodium hyaluronate 200 mg-23 mg DR capsule, administered as a single oral dose of 2 capsules under fasting conditions; Treatment B: mesalamine 200 mg DR capsule, administered as a single oral dose of 2 capsules under fasting conditions; and Treatment C: DELZICOL® 400 mg DR capsule, administered as a single oral dose of 1 capsule under fasting conditions). The trial was a single center, randomized, single-dose, open-label, 3-period, 6-sequence, crossover bioavailability (BA) study. A total of 30 healthy, adult subjects were enrolled. Prior to study commencement, subjects were randomly assigned to a treatment in accordance with the randomization scheme. The treatment phases were to be separated by washout periods of at least 14 days.

For mesalamine, blood samples were drawn into blood collection tubes (1×3 mL) containing EDTA $K_3$ prior to drug administration and 2, 4, 6, 7.5, 9, 10, 11, 12, 13, 14, 16, 18, 21, 24, 27, 30, 36, 48, 60, 72, and 96 hours post-dose on Days 1 to 5. For HA (Treatment A only), blood samples were drawn into plastic serum spray-coated silica collection tubes (1×3 mL)−1 hour, −0.5 hour, and within 5 minutes (0 hour) prior to drug administration and 2, 4, 6, 7.5, 9, 10, 11, and 12 hours postdose on Day 1. The −1 hour, and −0.5 hour were collected within +10 minutes of the nominal time, whenever possible. Actual post-dose sampling times were used for statistical analyses.

For mesalamine, blood samples were cooled in an ice bath and centrifuged at 3,000 rpm for at least 10 minutes at approximately 4° C. (no more than 240 minutes passes between the time of each blood draw and the start of centrifugation). Two aliquots of at least 0.5 ml (when possible) of plasma were dispensed into polypropylene tubes as soon as possible. The aliquots were transferred to a −80° C. (−65° C. to −85° C.) freezer (no more than 180 minutes passes between the start of centrifugation and aliquot storage), pending analysis. For HA, blood samples were allowed to clot at room temperature for at least 30 minutes following collection prior to being centrifuged at 2400 rpm for at least 10 minutes at room temperature (no more than 60 minutes passed between the time of each blood draw and the start of centrifugation). Two aliquots of at least 0.5 mL (when possible) of serum were dispensed into polypropylene tubes as soon as possible. The aliquots were transferred to a −80° C. (−65° C. to −85° C.) freezer (no more than 120 minutes passed between the start of centrifugation and aliquot storage), pending shipment to the analytical facility.

The pharmacokinetic (PK) parameters assessed were generally standard and the blood sampling schedule was determined based on pre-clinical PK data. In addition to the usual PK parameters, partial AUCs ($AUC_{8-48}$, $AUC_{6-12}$, $AUC_{12-24}$, and $AUC_{refTmax}$) were also to be calculated in this study for all treatment groups, in an attempt to compare thoroughly drug absorption (and therefore drug availability) at the site of action in the colon. Data were analyzed using analysis of variance (ANOVA). The quantitative data are presented as mean±standard deviation.

Formulation

Capsules formulations for use in the treatments A and B were prepared using conventional manufacturing processes to form multi-layered particles. Each capsule of treatment A contains:

(1) inert core: about 80 mg spherical starter pellets consisting of microcrystalline cellulose (CELLETS® 500);

(2) mesalamine layer: about 200 mg mesalamine, about 15 mg hydroxypropyl methylcellulose (hypromellose 2910), and about 8 mg talc;

(3) hyaluronan layer: about 18.4 mg HMWHA (2180 kDa), about 4.6 mg LMWHA (380 kDa), about 16.75 mg low-substituted hydroxypropyl cellulose;

(4) isolation layer: about 9 mg methacrylic acid-methyl methacrylate copolymer (EUDRAGIT® L100), about 5 mg talc, about 1 mg triethyl citrate;

(5) enteric coating layer: about 67 mg methyl acrylate-methyl methacrylate-methacrylic acid copolymer (EUDRAGIT® FS 30 D), about 7.5 mg methacrylic acid-ethyl acrylate copolymer (EUDRAGIT® L30D-55), about 7.5 mg lubricant/glidant premix containing triethyl citrate, glycerin monostearate, and sorbitol (PLASACRY® T20).

Each capsule of treatment B contains the same ingredient of the capsule of treatment A, excluding the hyaluronan layer.

Results

Figure 1B:
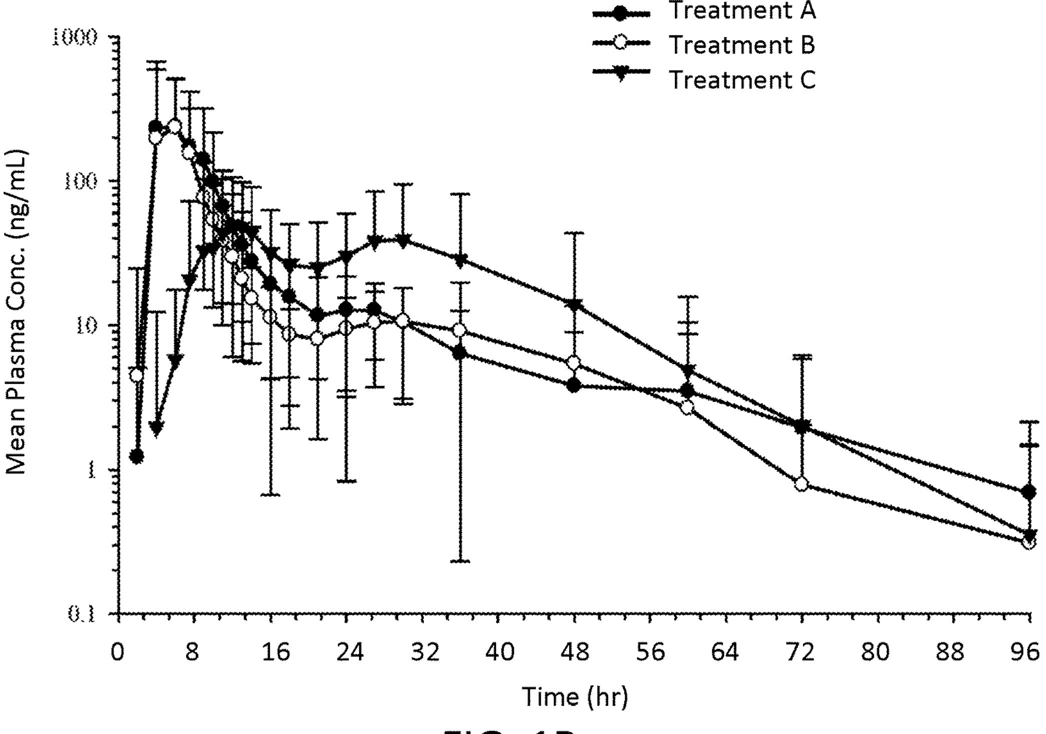

Mean±SD (CV %) of plasma mesalamine PK parameters are summarized in the Tables 1 below, and the mean plasma mesalamine concentration vs. time profile in the linear scale and log scale are shown in FIG. 1A and FIG. 1B, respectively.

TABLE 1

| Mean ± SD | Plasma Mesalamine | | |
|---|---|---|---|
| (CV %) | Treatment A | Treatment B | Treatment C[e] |
| N | 28[e] | 29 | 28[f] |
| $AUC_{0-t}$ (ng*hr/mL) | 2010.47 ± 1220.12 (60.69) | 1655.04 ± 1356.92 (81.99) | 1394.61 ± 1205.00 (86.40) |
| $AUC_{0-inf}$ (ng*hr/mL) | 2179.02 ± 1235.63 (56.71)[b] | 1930.74 ± 1431.25 (74.13)[c] | 1670.74 ± 1206.73 (72.23)[d] |
| $C_{max}$ (ng/ml) | 448.81 ± 436.56 (97.27) | 362.36 ± 408.30 (112.68) | 111.88 ± 76.63 (68.49) |
| $AUC_{8-48}$ (ng*hr/mL) | 827.25 ± 520.55 (62.93) | 597.82 ± 324.72 (54.32) | 1213.52 ± 1050.43 (86.56) |
| $AUC_{6-12}$ (ng*hr/mL) | 800.57 ± 795.60 (99.38) | 614.35 ± 494.05 (80.42) | 179.39 ± 276.29 (154.02) |
| $AUC_{12-24}$ (ng*hr/mL) | 233.66 ± 146.59 (62.73) | 141.25 ± 74.68 (52.87) | 388.28 ± 307.65 (79.23) |
| $AUC_{refTmax}$ (ng*hr/mL) | 1575.17 ± 1237.90 (78.59) | 1295.22 ± 1349.59 (104.20) | 284.02 ± 343.60 (120.98) |
| Residual Area (%) | 3.14 ± 3.56 (113.56)[b] | 5.12 ± 5.40 (105.31)[c] | 7.40 ± 9.34 (126.24)[d] |
| $T_{lag}$[a] (hr) | 2.00 (0.00-4.00) | 2.01 (0.00-4.03) | 7.50 (2.00-14.0) |
| $T_{max}$[a] (hr) | 6.00 (3.99-59.7) | 6.00 (4.00-9.00) | 14.00 (7.50-59.9) |

[a]Median (Min-Max)
[b]n = 25, Subject 1, 6, 15 not included in calculation of summary statistics
[c]n = 23, Subject 1, 7, 17, 19, 23, 27 not included in calculation of summary statistics
[d]n = 24, Subject 1, 11, 13, 22 not included in calculation of summary statistics
[e]Profile of Subject 12 was excluded
[f]Profile of Subject 17 was excluded The mean Residual area for mesalamine was less than 20% for all treatments indicating that a sampling over a period of 96 hours was sufficient for mesalamine. This is equivalent to a mean $AUC_{0-t}$ to $AUC_{0-inf}$ ratio above 80%.

The least-squares means ratios (A/C) of the Treatment A (the mesalamine-sodium hyaluronate 200 mg-23 mg DR capsule) to Treatment C (DELZICOL®) of In-transformed $AUC_{0-t}$, $AUC_{0-inf}$, $C_{max}$, $AUC_{6-12}$, $AUC_{12-24}$, $AUC_{8-48}$, and $AUC_{refTmax}$ were respectively 169.76%, 141.73%, 313.27%, 4492.78%, 70.52%, 73.82%, and 1471.09%.

The least-squares means ratios (A/C) of $AUC_{6-12}$ indicates that Treatment A provides over 40 times greater drug exposure between 6 to 12 hours after administration compared to Treatment C. The colon transit time for oral drugs is usually between 4 to 8 hours post-administration. Since Treatment A demonstrates an extremely high $AUC_{6-12}$ over Treatment C (4492.78%), this suggests that a large portion of the drug is being released during this critical window when the formulation is likely to be present in the colon. By delivering a high concentration of mesalamine during the 6 to 12-hour window, Treatment A can exert a stronger local anti-inflammatory effect in the colon. This is crucial for the treatment of inflammatory bowel diseases like ulcerative colitis, where localized action in the inflamed regions of the colon is required.

Furthermore, Treatment A achieves a significantly higher $C_{max}$ compared to Treatment C, more than three times higher (313.27%). This, in combination with a $T_{max}$ of 6 hours of Treatment A, suggests that Treatment A delivers a more concentrated amount of mesalamine to the bloodstream once it reaches the colon, which can be particularly beneficial in situations where rapid symptom relief is needed. For patients experiencing acute flares of ulcerative colitis, having a formulation that provides fast onset of action is a critical advantage, as it can help reduce inflammation and discomfort more quickly than a formulation with slower release (like Treatment C).

Additionally, Treatment A also results in higher $AUC_{0-t}$ (169.76%) and $AUC_{0-inf}$ (141.73%), compared to Treatment C, indicating that it provides higher total drug absorption compared to Treatment C. This suggests that Treatment A ensures greater systemic exposure, which may lead to a more robust therapeutic effect overall. Higher systemic absorption may be particularly important for severe cases of ulcerative colitis, where deeper layers of the intestinal tissue are affected and higher mesalamine levels are needed to adequately control the inflammation.

In summary, Treatment A demonstrates statistical superiority over Treatment C in terms of multiple pharmacokinetic parameters (including $C_{max}$, $AUC_{0-t}$, $AUC_{0-inf}$, and $AUC_{6-12}$), providing evidence that it delivers mesalamine more efficiently and in greater amounts than Treatment C. Therefore, the present delayed-release formulation (the mesalamine-sodium hyaluronate 200 mg-23 mg DR capsule) is better equipped to manage ulcerative colitis, particularly in scenarios requiring rapid drug availability and robust therapeutic coverage.

The least-squares means ratios (B/A) of Treatment B (the mesalamine 200 mg DR capsule) to Treatment A (the mesalamine-sodium hyaluronate 200 mg-23 mg DR capsule) of In-transformed $AUC_{0-t}$, $AUC_{0-inf}$, $C_{max}$, $AUC_{6-12}$, $AUC_{12-24}$, $AUC_{8-48}$, and $AUC_{refTmax}$ were respectively 72.64%, 81.95%, 81.21%, 73.52%, 63.97%, 75.00%, and 70.15%.

These results suggest that Treatment A is also superior to Treatment B for treating inflammatory bowel disease in terms of multiple PK parameters (including $C_{max}$, $AUC_{0-t}$, $AUC_{0-inf}$, and $AUC_{6-12}$). These parameters indicate better drug delivery and therapeutic action in the colon, the target site for inflammatory bowel disease treatment. The inclusion of a hyaluronan layer between the outer coating layer and mesalamine layer helps fine-tune the release profile of mesalamine, ensuring more controlled and sustained delivery specifically in the colon. The hyaluronan layer also provides additional protection to the mesalamine layer, preventing premature drug release in the upper GI tract (particularly in the stomach), ensuring more mesalamine reaches the inflamed areas of the colon. Moreover, hyaluronic acid itself has known anti-inflammatory effects that could further benefit the treatment of colonic inflammation, potentially enhancing the therapeutic effect of mesalamine.

It will be understood that the above description of embodiments is given by way of example only and that various modifications may be made by those with ordinary skill in the art. The above specification, examples, and data provide a complete description of the structural and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A delayed-release formulation, comprising a plurality of particles, wherein each particle comprises:

(a) an inert core, in an amount of 10-20 wt % of the particle;

(b) a mesalamine layer applied to the surface of the inert core, wherein the mesalamine layer is in an amount of 40-65 wt % of the particle and comprises mesalamine in an amount of 80-99 wt % of the mesalamine layer;

(c) a hyaluronan layer applied to the surface of the mesalamine layer, wherein the hyaluronan layer is in an amount of 3-15 wt % of the particle and comprises a high molecular weight hyaluronic acid or a pharmaceutically-acceptable salt thereof and a low molecular weight hyaluronic acid or a pharmaceutically-acceptable salt thereof in a ratio of 5:1 to 1:5, and the total hyaluronic acid or a pharmaceutically-acceptable salt is in an amount of 51-70 wt % of the hyaluronan layer; and (d) an isolation layer, applied to the surface of the hyaluronan layer, and comprising one or more copolymers selected from the group consisting of a methacrylic acid-methyl methacrylate copolymer, methacrylic acid-methacrylate copolymer, and a methacrylic acid-ethylacrylate copolymer; and (e) an enteric coating layer, applied to the surface of the isolation layer and comprising one or more copolymers selected from the group consisting of a methyl acrylate-methyl methacrylate-methacrylic acid copolymer, a methacrylic acid-methyl methacrylate copolymer, a methacrylic acid-ethyl acrylate copolymer, and a methacrylic acid-ethyl acetate copolymer, wherein the combined amount of the isolation layer and the enteric coating layer is 15-30 wt % of the particle.

2. The delayed-release formulation of claim 1, wherein the inert core comprises a filler selected from the group consisting of starch, sugar, microcrystalline cellulose, vegetable gums, and waxes.

3. The delayed-release formulation of claim 1, wherein the mesalamine layer further comprises at least one binder in an amount of 0.5-15 wt % of the mesalamine layer and selected from the group consisting of hydroxypropyl methylcellulose, hydroxypropyl cellulose, carboxymethyl-cellulose sodium, povidone, copolyvidone magnesium stearate, calcium stearate, zinc stearate, stearic acid, hydrogenated vegetable oil, hydrogenated castor oil, glyceryl palmitostearate, glyceryl behenate, polyethylene glycols, corn starch, sodium stearyl fumarate, sodium benzoate, mineral oil, talc, colloidal silicon dioxide, magnesium trisilicate, powdered cellulose, starch, tribasic calcium phosphate and mixtures thereof.

4. The delayed-release formulation of claim 1, wherein the high-molecular weight of hyaluronic acid or the pharmaceutically-acceptable salt thereof has a viscosity average molecular weight of 2000 kDa to 2500 kDa, and the low-molecular weight of hyaluronic acid or the pharmaceutically-acceptable salt thereof has a viscosity average molecular weight of 300 kDa to 500 kDa.

5. The delayed-release formulation of claim 1, wherein the hyaluronan layer further comprises at least one binder in an amount of 30-49 wt % of the hyaluronan layer and selected from the group consisting of hydroxypropyl methylcellulose, hydroxypropyl cellulose, carboxymethyl-cellulose sodium, povidone, copolyvidone magnesium stearate, calcium stearate, zinc stearate, stearic acid, hydrogenated vegetable oil, hydrogenated castor oil, glyceryl palmitostearate, glyceryl behenate, polyethylene glycols, corn starch, sodium stearyl fumarate, sodium benzoate, mineral oil, talc, colloidal silicon dioxide, magnesium trisilicate, powdered cellulose, starch, tribasic calcium phosphate and mixtures thereof.

6. The delayed-release formulation of claim 1, wherein the enteric coating layer further comprises at least one plasticizer selected from the group consisting of acetyltributyl citrate, acetyltriethyl citrate, benzyl benzoate, cellulose acetate phthalate, chlorbutanol, dextrin, dibutyl phthalate, dibutyl secacate, diethyl phthalate, dimethyl phthalate, glycerin, glycerin monostearate, hypromellose phthalate, mannitol, mineral oil and lanolin alcohols, palmitic acid, polyethylene glycol, polyvinyl acetate phthalate, propylene glycol, 2-pyrrolidone, sorbitol, stearic acid, triacetin, tributyl citrate, triethanolamine, and triethyl citrate.

7. The delayed-release formulation of claim 1, wherein the isolation layer further comprises at least one plasticizer selected from the group consisting of acetyltributyl citrate, acetyltriethyl citrate, benzyl benzoate, cellulose acetate phthalate, chlorbutanol, dextrin, dibutyl phthalate, dibutyl secacate, diethyl phthalate, dimethyl phthalate, glycerin, glycerin monostearate, hypromellose phthalate, mannitol, mineral oil and lanolin alcohols, palmitic acid, polyethylene glycol, polyvinyl acetate phthalate, propylene glycol, 2-pyrrolidone, sorbitol, stearic acid, triacetin, tributyl citrate, triethanolamine, and triethyl citrate.

8. The delayed-release formulation of claim 1, wherein the plurality of particles are filled into a capsule, pouch, packet, sachet, bottle, or blister pack.

9. A method of treating inflammatory bowel disease, comprising administering to a patient in need of such treatment an effective amount of a delayed-release formulation according to claim 1.

10. The method of claim 9, wherein the hyaluronan layer comprises a high-molecular weight of hyaluronic acid or the pharmaceutically-acceptable salt thereof and a low-molecular weight of hyaluronic acid or the pharmaceutically-acceptable salt thereof in an amount of 1:5 to 5:1.

11. The method of claim 9, wherein the plurality of particles are filled into a capsule, pouch, packet, sachet, bottle, or blister pack.

* * * * *